US006613349B2

(12) United States Patent
Ford et al.

(10) Patent No.: US 6,613,349 B2
(45) Date of Patent: *Sep. 2, 2003

(54) ADMINISTRATION OF OXAZOLIDINONES FOR TRANSDERMAL DELIVERY

(75) Inventors: Charles W. Ford, Portage, MI (US); Jeffrey L. Watts, Portage, MI (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/320,428

(22) Filed: May 26, 1999

(65) Prior Publication Data

US 2002/0009483 A1 Jan. 24, 2002

Related U.S. Application Data

(63) Continuation of application No. 09/320,428, filed on May 26, 1999.
(60) Provisional application No. 60/088,283.

(51) Int. Cl.$^7$ .......................... A61F 13/00; A61L 15/16
(52) U.S. Cl. ...................... 424/449; 424/443; 424/448
(58) Field of Search ...................... 424/443; 514/235.5, 514/230.2, 376, 312

(56) References Cited

U.S. PATENT DOCUMENTS

| 3,743,727 | A | | 7/1973 | Herschler, et al. | 424/181 |
|---|---|---|---|---|---|
| 4,923,862 | A | | 5/1990 | Hirota | 514/230.2 |
| 4,943,435 | A | | 7/1990 | Baker et al. | 424/448 |
| 5,164,510 | A | | 11/1992 | Brickner | 548/231 |
| 5,231,188 | A | | 7/1993 | Brickner | 548/221 |
| 5,247,090 | A | * | 9/1993 | Brickner | 546/89 |
| 5,254,577 | A | * | 10/1993 | Carlson et al. | 514/376 |
| 5,457,194 | A | * | 10/1995 | Luly et al. | 540/456 |
| 5,565,571 | A | | 10/1996 | Barbachyn et al. | 546/144 |
| 5,627,181 | A | | 5/1997 | Riedl et al. | 514/236.8 |
| 5,652,238 | A | | 7/1997 | Brickner et al. | 514/235.8 |
| 5,688,792 | A | * | 11/1997 | Barbachyn et al. | 514/235.5 |
| 5,698,574 | A | | 12/1997 | Riedl et al. | 514/376 |
| 5,922,707 | A | * | 7/1999 | Thomas et al. | 514/230.2 |
| 5,929,086 | A | * | 7/1999 | Watts et al. | 514/312 |
| 6,040,306 | A | * | 3/2000 | Batts et al. | |
| 6,174,878 | B1 | * | 1/2001 | Gamache et al. | |
| 6,191,143 | B1 | | 2/2001 | Watts et al. | 514/312 |

FOREIGN PATENT DOCUMENTS

| WO | WO 85/00108 | 1/1985 | .......... A61K/31/70 |
|---|---|---|---|
| WO | WO 90/00407 | 1/1990 | .......... A61K/47/22 |
| WO | WO 96/08229 | 3/1996 | |
| WO | WO 97/42954 | 11/1997 | .......... A61K/31/47 |
| WO | WO 99/56782 | 11/1999 | .......... A61K/47/30 |

OTHER PUBLICATIONS

Jia–You Fang, et al., *Effect of liposomes and niosomes on skin permeation of enoxacin*, International Journal of Pharmaceutics, 219 (2001). pp 61–72.

Pfister, W., et al: "Oxazolidinones: A new class of cyclic urethane transdermal enhancer (CUTE)" Proc. Int'l Symp. Control. Rel. Bioact Mater. vol. 24, 1997, pp. 709–710, XP000853932.

* cited by examiner

Primary Examiner—Thurman K. Page
Assistant Examiner—Isis Ghali
(74) Attorney, Agent, or Firm—Mary J. Hosley

(57) ABSTRACT

Disclosed is a method of treating a non-topical infection selected from the group consisting of ear infections, skin and soft tissue infections, acne, infected wounds, bacteremia, in a useful warm blooded mammal who is in need of such treatment which comprises topical administration of a pharmaceutical formulation containing a transdermally effective amount of an Oxazolidinone.

14 Claims, No Drawings

ADMINISTRATION OF OXAZOLIDINONES FOR TRANSDERMAL DELIVERY

CROSS-REFERENCE TO RELATED APPLICATIONS

This continuation application claims the benefit of US provisional application Ser. No. 60/088,283 filed Jun. 5, 1998, under 35 USC §119(e)(i), and is a continuation of the non-provisional application having Ser. No. 09/320,428 filed May 26, 1999.

BACKGROUND OF THE INVENTION

1. Field of the Invention

The present invention is a method of treating topical application of known pharmaceutically useful Oxazolidinone antibacterials to treat non-topical infections.

2. Description of the Related Art

U.S. Pat. Nos. 5,164,510, 5,231,188, 5,565,571, 5,652,238, 5,688,792, 5,698,574 and 5,627,181 all disclose various oxazolidinone antibiotics which are well known to those skilled in the art.

U.S. Pat. No. 5,688,792 discloses various oxazolidinone antibiotics which can be administered orally, parenterally or topically. The topical application being by gel or cream vehicle.

PCT patent application PCT/US97/07124 published as International Publication WO97/42954 discloses a method of transdermal administration of a number of antimicrobial agents for treating or preventing systemic bacterial diseases which comprised use of DMSO/water carrier which comprised at least 10% DMSO. None of the antimicrobial agents of International Publication WO97/42954 included Oxazolidinones and the present invention does not use any DMSO.

U.S. Pat. No. 3,743,727 discloses a method of enhancing the penetration into and across the external membrane barrier of an animal subject of an antimicrobial agent of various types which comprised sufficient DMSO to sufficiently enhance the penetration of the antimicrobial agent. None of the antimicrobial agents included oxazolidinones and the present invention does not use any DMSO.

PCT patent application PCT/US84/00899 published as International Publication WO85/00108 discloses a method of treating acne with topical preparations comprising an antibacterial agent in DMSO. None of the antibacterial agents included oxazolidinones and the present invention does not use any DMSO.

U.S. Pat. No. 4,943,435 discloses a transdermal patch for controlled delivery of nicotine. This is a small molecule and not an antibacterial agent.

SUMMARY OF INVENTION

Disclosed is a method of treating a non-topical infection selected from the group consisting of ear infections, skin and soft tissue infections, acne, infected wounds, bacteremia, in a useful warm blooded mammal who is in need of such treatment which comprises topical administration of a pharmaceutical formulation containing a transdermally effective amount of an Oxazolidinone.

DETAILED DESCRIPTION OF THE INVENTION

U.S. Pat. No. 5,688,792 which disclosed various oxazolidinone antibiotics disclosed they could be administered orally, parenterally or topically. Topical administration is not specifically defined but used in its ordinary meaning. Dorland's Illustrated Medical Dictionary (twenty-sixth edition, 1981, page 1377) defines topical as, "pertaining to a particular surface area, as a topical anti-infective applied to a certain area of the skin and affecting only the area to which it is applied." Therefore, topical administration is administration to a certain area of the skin where the applied item only affects the area to which it is applied. This differs significantly from transdermal. Topical differs from transdermal in that transdermal administration refers to topical administration of an agent, for the purpose of delivering the agent to an adjacent, underlying or distant site or tissue which is different than the site of application. With the Oxazolidinones of the present invention, it is understood that the topical application is to the top of the skin which is not the site of antibacterial activity, which is below or away from the site of topical application. The Oxazolidinone may have antibacterial activity at the top of the skin where [applied] it is applied but that is incidental to the site of intended action. The infection being treated is a non-topical infection.

The claimed invention is a method of treating an infection selected from the group consisting of ear infections, skin and soft tissue infections, acne, infected wounds, bacteremia, in a useful warm blooded mammal who is in need of such treatment which comprises topical administration of a transdermally effective amount of an Oxazolidinone.

Useful warm blooded mammals which are within the scope of the present invention include humans, pets such as dogs, cats and commercially important mammals such as horses, cattle, pigs. It is preferred that the mammal be a human, dog or cat; more preferably a human.

The Oxazolidinones of the present invention are known, see EXAMPLES 1 thru 6 (Oxazolidinones). It is preferred that the Oxazolidinone be selected from the group consisting of:

(S)-N-[[3-[3-fluoro-4-[4-(hydroxyacetyl)-1-piperazinyl]-phenyl]-2-oxo-5-oxazolidinyl]methyl]acetamide, (S)-N-[[3-[3-fluoro-4-(4-morpholinyl)phenyl]-2-oxo-5-oxazolidinyl]methyl]acetamide,

[4(S)-cis]-(−)-N-[[3-[3-fluoro-4-(tetrahydro-1-oxido-2H-thiopyran-4-yl)phenyl]-2-oxo-5-oxazolidinyl]methyl]acetamide, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide and (S)-N-[[3-[5-(4-pyridyl)pyrid-2-yl]-2-oxo-5-oxazolidinyl]methyl]acetamide hydrochloride. It is more preferred that the Oxazolidinone be selected from the group consisting of:

(S)-N-[[3-[3-fluoro-4-[4-(hydroxyacetyl)-1-piperazinyl]-phenyl]-2-oxo-5-oxazolidinyl]methyl]acetamide, (S)-N-[[3-[3-fluoro-4-(4-morpholinyl)phenyl]-2-oxo-5-oxazolidinyl]methyl]acetamide and

[4(S)-cis]-(−)-N-[[3-[3-fluoro-4-(tetrahydro-1-oxido-2H-thiopyran-4-yl)phenyl]-2-oxo-5-oxazolidinyl]methyl]acetamide; and it is even more preferred that the Oxazolidinone be (S)-N-[[3-[3-fluoro-4-(4-morpholinyl)phenyl]-2-oxo-5-oxazolidinyl]methyl]acetamide.

The infections treated by the present invention include ear infections, skin and soft tissue infections, acne, infected wounds and bacteremia which are not topical infections but rather infections of the underlying tissue.

Ear infections can be caused by either gram positive or gram negative bacteria or mixture of both. About 60% of the time, the ear infection is caused by gram positive bacteria and in those cases the method of the present invention will be useful in treating the ear infection. If not treated successfully, the two important consequences are the ear drum can rupture leading to a reduction in hearing, and the surrounding tissues including bone can become infected and lead to a more life threatening condition. Ear infections are most often caused by *Streptococcus pneumoniae* and sometimes by *Streptococcus pneumoniae* and *Haemophilus influenzae* at the same time. It is apparent to one skilled in the art that a subject is in need of treatment for an ear infection when there is a fever and the patient has pain in the ear or the patient has pain in the ear and an ear exam discloses a swollen ear rum and fluid is observed behind the ear drum. Ear infections are treated by administering the desired Oxazolidinone(s) directly to the affected ear by use of a pharmaceutical formulation which is a solution, suspension or emulsion. It is preferred that the transdermally effective amount of the Oxazolidinone for treatment of ear infections is from about 0.1 to about 10%; it is more preferred that the transdermally effective amount is from about 0.2 to about 2%. The Oxazolidinone should be administered two thru four times daily for 3 to 14 days. It is preferable if 0.25 to 1 ml of the pharmaceutical formulation is containing the Oxazolidinone is administered each time it is administered.

Skin and soft tissue infections are infections which are most often caused by staphylococci and streptococci. Such infections are very difficult to treat with known antibiotics because of their location and treatment failures occur often requiring additional courses of therapy. These infections include skin (cellulitis and superficial infections) and skin-associated soft tissue infections (subcutaneous tissue infections and abscesses as well as myostis) where the (gram positive) bacteria are present in the epidermis, dermis, fat layer and/or muscle layers underlying the epidermis. It is apparent to one skilled in the art that a subject is in need of treatment for a soft tissue and/or skin infection when the subject has an inflamed, reddened, or tender area of the body which is coupled with a fever. The skin and soft tissue infections are treated by administering the desired Oxazolidinone(s) directly to a site such that the affected area is adjacent, underlying or distant from the site of application by use of the appropriate pharmaceutical dosage form. It is preferred that the Oxazolidinone be administered in the form of a pharmaceutical formulation which is a cream, ointment, gel and emulsion and it is preferred that the pharmaceutical formulation be applied or administered two thru four times daily, preferably two or three times daily until 24 after the fever is at normal and the redness, swelling and inflammation are gone. It is preferred that the transdermally effective amount to treat skin and soft tissue infections be from about 0.2 to about 40%; more preferably from about 0.4 to about 10%. Other sanitary precautions should be utilized as are known to those skilled in the art.

Acne refers to acne serious enough to be treated by a physician, termed acne vulgaris. Acne vulgaris is caused by the anaerobic bacterium *Propionibacterium acnes* which is found in blocked and inflamed oil glands or ducts in the skin of humans, particularly teenagers. These infections occur well below the surface of the skin and need to be treated at that area. While not life threatening, serious acne can cause both skin scars and emotional trauma. It is preferred that the acne be treated with a pharmaceutical formulation which is a cream, ointment, gel, emulsion, suspension, solution and patch. The transdermal effective amount of the Oxazolidinone is preferably from about 0.1 to about 10%; more preferably from about 0.2 to about 6%. The acne is treated two thru four times daily until the acne is contained to the satisfaction of the patient and treating physician.

Wounds refer to and include wounds caused by natural causes such as accidents and intentional wounds such as those caused by surgery. Because of the opening into the body, as in a penetrating wound, gram positive microorganism often are able to get in and cause an infection. These infections can be very serious and even life threatening. Because the Staphaphlococcus organisms are on our skin, once a wound occurs, regardless of the cause, these microorganisms enter the body thru the wound. By definition the wound is not just on the surface, but includes the underlying infected area below the skin. The wound is treated two thru four times daily until the infection is gone.

Bacteremia is an infection where bacteria are present in the blood and can be microbiologically cultured from blood samples. Bacteremia is caused by the gram positive organisms identified in this patent are preferably treated with pharmaceutical compositions of Oxazolidinone including cream, ointment, gel, emulsion and suspension. It is preferred that the transdermal effective amount is from about 1 to about 40%; it is more preferred that the transdermal effective amount is from about 5 to about 20%. The bacteremia infection is treated twice to four times daily until the infection is gone.

The gram positive microorganisms which cause the infections treated by the Oxazolidinones of the present invention include Staphylococci, Streptococci and Enterococci. It is preferred that the infection be caused by Staphyloccoci. The important species of these genius are *Staphloccus aureus, Staphloccus epidermidis* and *Staphyloccus hemolyticus*. The Oxazolidinones of the present invention also treat gram negative infections caused by anaerobes such as *Bacteroides fragilis*.

By "treating an infection" selected from the group consisting of ear infections, skin and soft tissue infections, acne, infected wounds and bacteremia in a useful warm blooded mammals who is in need of such treatment, means the mammal has an infection which is causing it a problem, whether a fever, pain such as ear ache, abscess, infection and inflammation of a tissue or a wound. Treating the infection means administering to the mammal an Oxazolidinone such that the mammal obtains sufficient concentration of the Oxazolidinone in the affected area to either kill the existing microorganisms and/or to reduce their rate of multiplication (increase) to a point where the body's natural defense mechanism can reduce the unwanted microorganisms to a level which does not cause clinical problems. "Treating" also includes preventing an infection, or preventing a minor infection to grow into a larger one especially with acne. Even though the patient may not observe blocked or inflamed oil glands or ducts, they may still be present but at a greatly reduced stage. Treating a teenager who has had acne to prevent future occurrence is included within the scope of "treating" as used in this patent.

In the method of the present invention, the Oxazolidinones can be used either individually or in combination with each other. Further, they can be used in combination with other antibacterial agents which are being administered by oral administration. In addition, the Oxazolidinones can be used with non-antibacterial agents in treating the infections of this invention.

The exact dosage and frequency of administration depends on the particular Oxazolidinone used, the particular condition being treated, the severity of the condition being treated, the age, weight, general physical condition of the particular patient, other, medication the individual may be taking as is well known to those skilled in the art and can be more accurately determined by measuring the blood level or concentration of the Oxazolidinone in the patient's blood and/or the patient's response to the particular condition being treated.

DEFINITIONS AND CONVENTIONS

The definitions and explanations below are for the terms as used throughout this entire document including both the specification and the claims.

DEFINITIONS

All temperatures are in degrees Centigrade.

THF refers to tetrahydrofuran.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

Ether refers to diethyl ether.

TLC refers to thin-layer chromatography.

When solvent pairs are used, the ratios of solvents used are volume/volume (v/v).

When the solubility of a solid in a solvent is used the ratio of the solid to the solvent is weight/volume (wt/v).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Oxazolidinone refers to the compounds of EXAMPLES 1 thru 6 of the present invention.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

(S)-N-[[3-[3-Fluoro-4-[4-(hydroxyacetyl)-1-piperazinyl]-phenyl]-2 oxo-5-oxazolidinyl]methyl] acetamide (S)-N-[[3-[3-Fluoro-4-[4-(hydroxyacetyl)-1-piperazinyl]-phenyl] -2-oxo-5-oxazolidinyl]methyl]acetamide is known, see U.S. Pat. No. 5,652,238, EXAMPLE 1.

Example 2

(S)-N-[[3-[3-Fluoro-4-(4-morpholinyl)phenyl]-2-oxo-5-oxazolidinyl]methyl]acetamide (S)-N-[[3-[3-Fluoro-4-(4-morpholinyl)phenyl]-2-oxo-5-oxazolidinyl]methyl]acetamide is known, see U.S. Pat. No. 5,688,792, EXAMPLE 5.

Example 3

[4(S)-cis]-(−)-N-[[3-[3-Fluoro-4-(tetrahydro-1-oxido-2-H-thiopyran-4-yl)phenyl]-2-oxo-5-oxazolidinyl]methyl]acetamide A mixture of (S)-(−)-N-[[3-[3-fluoro-4-(3,6-dihydro-2-H-thiopyran-4-yl)phenyl]-2-oxo-5-oxazolidinyl]methyl] acetamide S-oxide (International Publication No. WO97/09328, 4.50 g) and platinum oxide (697 mg) in methanol (164 ml) is shaken on the Parr apparatus under a hydrogen atmosphere at 40 psi for 18 hours. The catalyst is then removed by filtration through Celite, and the filtrate is concentrated under reduced pressure and the residue chromatographed on silica gel (230–400 mesh, 350 g), eluting with a gradient of methanol/methylene chloride (3/97–7/93). The appropriate fractions (those fractions with an $R_f$=0.44 by TLC; methanol/chloroform, 10/90) are pooled and concentrated to give the title compound, mp=203–204°.

Example 4

N-((5-S)-3-(3-Fluoro-4-(4-(2-fluoroethyl)-3-oxopiperazin-1-yl)phenyl)-2-oxooxazolidin-5-ylmethyl)acetamide N-((5 S)-3-(3-Fluoro-4-(4-(2-fluoroethyl)-3-oxopiperazin-1-yl)phenyl)-2-oxooxazolidin-5-ylmethyl) acetamide is known, see International Publication WO97/27188 (Example 4).

1-t-Butoxycarbonyl-3-oxopiperazine (21.6 g) is dissolved in dry DMF (500 ml) and potassium t-butoxide (24.2 g) is added. The mixture is stirred at 20–25° for 30 minutes, then 1-(4-methylphenylsulfonyloxy)-2-fluoroethane (*J. Med. Chem.*, 23(9), 985–90 (1980), 25.9 g) is added and stirring continued at the same temperature for 24 hours. The solvent is removed and the residue partitioned between ethyl acetate and water. The organic phase is washed with water and concentrated. The residue is dissolved in isopropanol and diluted with iso-hexane forming a precipitate which is removed by filtration. The mixture is chromatographed (silica; eluting with a gradient increasing in polarity from 0 to 50% isopropanol in iso-hexane) to give 1-t-butoxycarbonyl-4-(2-fluoroethyl)-3-oxopiperazine.

1-t-Butoxycarbonyl-4-(2-fluoroethyl)-3-oxopiperazine (6.65 g) is dissolved in dichloromethane (500 ml), cooled in an ice-bath and trifluoroacetic acid (150 ml) added. The mixture is stirred at the same temperature for 2 hours. The solvent is removed to give a crude product which is dissolved in the minimum volume of ethyl acetate. Slow addition of ether causes precipitation of 1-(2-fluoroethyl)-2-oxopiperazine as the mono trifluoroacetic acid salt.

1-(2-Fluoroethyl)-2-oxopiperazine trifluoroacetate (6.1 g) is dissolved in acetonitrile (100 ml). N,N-Diisopropylethylamine (13 ml) is added to the mixture, followed by 3,4-difluoronitrobenzene (3.39 g) and the mixture heated to reflux for 18 hours. The solvent is removed and the residue chromatographed (silica; eluting with a gradient increasing in polarity from 0 to 4% methanol in dichloromethane) to give 3-fluoro-4-(4-{2-fluoroethyl}-3-oxopiperazin-1-yl)nitrobenzene.

3-Fluoro-4-(4-{2-fluoroethyl}-3-oxopiperazin-1-yl) nitrobenzene (4.35 g) is dissolved in a mixture of ethyl acetate (250 ml) and DMF (5 ml), and the solution flushed with argon. Palladium (10% on carbon, 200 mg) is added and the mixture hydrogenated under ambient pressure. After gas uptake had ceased, the mixture is filtered through celite and solvent removed. The residue is taken up in ethyl acetate, washed twice with water, dried over magnesium sulfate and the solvent is removed to give 5-amino-2-[4-(2-fluoroethyl)-3-oxopiperazin-1-yl]fluorobenzene which is used without further purification.

5-Amino-2-(4-[2-fluoroethyl]-3-oxopiperazin-1-yl) fluorobenzene (2.6 g) is dissolved in dry dichloromethane (50 ml) under argon. Pyridine (1.03 ml) is added, and the mixture cooled to −20°. Benzyl chloroformate (1.6 ml) is added and the mixture stirred for 10 minutes at −20°, before allowing the temperature to rise to 20–25° over 1.5 hours. The solvents are removed and the residue is dissolved in dichloromethane and washed with sodium bicarbonate solution. After drying over magnesium sulfate and removal of the solvent, the residue is chromatographed (silica, eluting with a gradient increasing in polarity from 0 to 5% methanol in dichloromethane) to give 5-benzyloxycarbonylamino-2-(4-[2 fluoroethyl]-3-oxopiperazin-1-yl)fluorobenzene.

A solution of lithium t-butoxide is prepared by addition of n-butyllithium (1.6 M in hexane, 2.9 ml) to a stirred solution of t-butanol (0.43 g) in anhydrous THF (10 ml) at −10° under argon. After cooling to −70°, a solution of 5-benzyloxycarbonylamino-2-(4-[2 fluoroethyl]-3-oxopiperazin-1-yl)fluorobenzene (1.5 g) in dry THF (15 ml) is added. After 10 minutes, (R)-glycidylbutyrate (0.67 g) in dry THF (15 ml) is added to the resulting mixture, and stirring continued at −70° for 15 minutes, before allowing the temperature to rise to 20–25° over 16 hours. Methanol (10 ml) is added, followed by saturated sodium bicarbonate solution (20 ml) and water (10 ml). The organic phase is separated and extracted into ethyl acetate (3×25 ml), washed with saline and dried over magnesium sulfate. The solvent is removed and the residue purified by chromatography (silica; eluting with a gradient increasing in polarity from 0 to 3% methanol in dichloromethane) to give (5R)-3-(3-fluoro-4-[4-(2-fluoroethyl)-3-oxopiperazin-1-yl]phenyl)-5 hydroxymethyloxazolidin-2-one.

(5R)-3-(3-Fluoro-4-[4-(2-fluoroethyl)-3-oxopiperazin-1-yl]phenyl)-5-hydroxymethyloxazolidin-2-one (0.8 g) is dissolved in pyridine (15 ml) and the mixture cooled to 0°. Triethylamine (0.38 ml) and methanesulfonyl chloride (0.19 ml) are added to the mixture, and stirring continued at 20–25° for 2 hours. The solvent is removed and the residue dissolved in dichloromethane, washed with water, saline, dried over magnesium sulfate and concentrated. The resulting residue is triturated with ether to give (5R)-3-(3-fluoro-4-[4-(2-fluoroethyl)-3-oxopiperazin-1-yl]phenyl)-5-(methanesulfonyloxymethyl)oxazolidin-2-one (0.76 g) which is used without further purification.

(5R)-3-(3-Fluoro-4-[4-(2-fluoroethyl)-3-oxopiperazin-1-yl]-5(methanesulfonyloxymethy)oxazolidin-2-one (719 mg) is dissolved in dry DMF (15 ml) and sodium azide (647 mg) is added to the mixture. The mixture is heated at 80° for 6 hrs and then concentrated to dryness. The resulting residue is dissolved in ethyl acetate, washed twice with water, and dried over magnesium sulfate. Removal of the solvent gives (5R)-5-azidomethyl-3-(3-fluoro-4-(4-(2-fluoroethyl)-3-oxopiperazin-1-yl)phenyl)oxazolidin-2-one (413 mg) which is used without further purification.

(5R)-5-Azidomethyl-3-(3-fluoro-4-[4-(2-fluoroethyl)-3-oxopiperazin-1-yl]phenyl)oxazolidin-2-one (360 mg) is dissolved in dry DMF (20 ml) and the mixture purged with argon. Palladium (10% on carbon, 72 mg) is added, followed by acetic anhydride (0.17 ml) and the mixture stirred at 20–25° under hydrogen confined in a balloon for 3 hr. The mixture is filtered through celite, concentrated to dryness and partitioned between ethyl acetate and water. The organic extract is washed with saline, dried over magnesium sulfate and concentrated. The residue is chromatographed (silica gel; eluting with a gradient increasing in polarity from 0 to 2.5% methanol/dichloromethane). The appropriate fractions are pooled and concentrated to give the title compound.

Example 5

-(S)-N-[[3-[5-(3-Pyridyl)thiophen-2-yl]-2-oxo-5-oxazolidinyl]methyl]acetamide (S)-N-[[3-[5-(3-Pyridyl)thiophen-2-yl]-2-oxo-5-oxazolidinyl]methyl]acetamide is known, see U.S. Pat. No. 5,698,574 (Example 124).

Example 6

(S)-N-[[3-[5-(4-Pyridyl)pyrid-2-yl]-2-oxo-5-oxazolidinyl]methyl]acetamide hydrochloride (S)-N-[[3-[5-(4-Pyridyl)pyrid-2-yl]-2-oxo-5-oxazolidinyl]methyl]acetamide hydrochloride is prepared following the general procedure of U.S. Pat. No. 5,627,181 Examples 36 and 52 and making non-critical variations but using a 4-pyridinyl adduct.

Example A

A Human who has Acne is Treated With an Oxazolidinone Ointment

A 14 year old 70 kilo male who has acne as evidenced by reddened and swollen pustules located over his face, neck, chest and back is treated by the administration of a ointment containing 30 mg/ml of (S)-N-[[3-[3-fluoro-4-[4-(hydroxyacetyl)-1-piperazinyl]phenyl]-2-oxo-5-oxazolidinyl]methyl]acetamide administered twice daily until the redness and swelling are gone. After administration of the Oxazolidinone, the reddened and swollen pustules are greatly reduced.

Example B

A Human who has an Ear Infection is Treated With Oxazolidinone Solution

A seven year old 28 kilo child has otitis media as evidence by the presence of a bulging ear drum with observed fluid behind it and has had a fever of 102° for two days. Ten drops of a solution containing 10 mg/ml of (S)-N-[[3-[3-fluoro-4-(4 morpholinyl)phenyl]-2-oxo-5-oxazolidinyl]methyl] acetamide is dropped into the ear twice daily for ten days with an eye dropper and is immediately followed by closing the outer ear canal with cotton. Before 10 days, the fever is down and the pain is gone.

Example C

Human with Post Surgical Wound Infection is Treated With an Oxazolidinone Cream

A 40 year old female is found to have an inflamed and reddened incision site one day following surgery accompanied by a fever of greater than 101°. The surgical dressings are removed and the incision site is covered with a cream which contains 15% of [4(S)-cis](−)-N-[[3-[3-fluoro-4-(tetrahydro-1-oxido-2 H-thiopyran-4-yl)phenyl]-2-oxo-5-oxazolidinyl]methyl]acetamide after which fresh dressings are applied. The cream is applied twice to three times daily until the fever has been normal for 24 hr and no signs of redness and tenderness persist.

Example D

Human with Wound Infection is Treated With Oxazolidinone Gel

A 22 year old 65 kg female who has a severely swollen and painful finger with a history of having punctured the finger on a rose thorn two days previously is treated by administering a gel containing 1% N-((5 S)-3-(3-fluoro-4-(4-(2-fluoroethyl)-3-oxopiperazin-1-yl)phenyl)-2-oxooxazolidin-5-ylmethyl)acetamide twice daily for 10 days. The site of inflammation is kept lightly covered with a sterile bandage following antibiotic therapy. The wound heals.

Example E

Human who has a Bacteremia Infection Treated With a Cream

A 46 year old 74 kg female who has bacteremia infection as measured by a temperature of greater than 101° for 3 days is treated by administering a cream containing 10% of (S)-N-[[3-[3-fluoro-4-[4-(hydroxyacetyl)-1-piperazinyl]-phenyl]-2-oxo-5 oxazolidinyl]methyl]acetamide. The cream is applied to both her arms twice a day until the fever is back to normal.

What is claimed is:

1. A method of treating soft tissue infections in a useful warm blooded mammal who is in need of such treatment which comprises administration of a pharmaceutical composition comprising a transdermally effective amount of an Oxazolidinone to the skin at a site that is not the site of infection, wherein the Oxazolidinone is selected from the group consisting of:

(S)-N-[[3-[3-fluoro-4-[4-(hydroxyacetyl)-1-piperazinyl]-phenyl]-2-oxo-5-oxazolidinyl]methyl]acetamide;

(S)-N-[[3-[3-fluoro-4-(4-morpholinyl)phenyl]-2-oxo-5-oxazolidinyl]methyl]acetamide;

[4(S)-cis]-(-)-N-[[3-[3-fluoro-4-(tetrahydro-1-oxido-2H-thiopyran-4-yl)phenyl]-2-oxo-5-oxazolidinyl]methyl] acetamide; and pharmaceutically acceptable salts thereof.

2. A method of treating a non-topical infection according to claim 1 where the useful warm blooded mammal is a human.

3. A method of treating a non-topical infection according to claim 1 where the useful warm blooded mammal is a dog or cat.

4. A method of treating a non-topical infection according to claim 1 where the pharmaceutical formulation is a cream, ointment, gel and emulsion.

5. A method of treating a non-topical infection according to claim 1 where the transdermally effective amount is where the cream, ointment, gel, or emulsion has a concentration of Oxazolidinone from about 0.2 to about 40%.

6. A method of treating a non-topical infection according to claim 5 where the transdermally effective amount is where the cream, ointment, gel, or emulsion has a concentration of Oxazolidinone from about 0.4 to about 10%.

7. A method of treating a non-topical infection according to claim 1 where the infection is caused by Staphylococci, Streptococci and Enterococci.

8. A method of treating a non-topical infection according to claim 7 where the infection is caused by Staphylococci.

9. A method of treating a non-topical infection according to claim 1 where the Oxazolidinone is:

(S)-N-[[3-[3-fluoro-4-(4-morpholinyl)phenyl]-2-oxo-5-oxazolidinyl]methyl]acetamide.

10. A method of treating a non-topical infection according to claim 1 where the Oxazolidinone is administered from 2 thru 4 times daily.

11. A method of treating a soft tissue infection according to claim 1 where the infection is diabetic foot.

12. A method of treating diabetic foot according to claim 1 where the pharmaceutical formulation is a cream, ointment, gel and emulsion.

13. A method of treating diabetic foot according to claim 12 where the transdermally effective amount is where the cream, ointment, gel, or emulsion has a concentration of Oxazolidinone from about 0.2 to about 40%.

14. A method of treating diabetic foot according to claim 13 where the transdermally effective amount is where the cream, ointment, gel, or emulsion has a concentration of Oxazolidinone from about 0.4 to about 10%.

* * * * *